United States Patent [19]

Francisco, Jr.

[11] Patent Number: 4,773,253

[45] Date of Patent: Sep. 27, 1988

[54] METHOD AND APPARATUS FOR MEASURING FLUID DENSITY

[75] Inventor: Edward E. Francisco, Jr., Paradise Valley, Ariz.

[73] Assignee: Flow Technology, Inc., Phoenix, Ariz.

[21] Appl. No.: 110,108

[22] Filed: Oct. 15, 1987

Related U.S. Application Data

[63] Continuation of Ser. No. 046,138, May 4, 1987, abandoned, which is a continuation-in-part of Ser. No. 811,719, Dec. 20, 1985, abandoned.

[51] Int. Cl.⁴ ............................................. G01N 9/32
[52] U.S. Cl. .................................................. 73/32 R
[58] Field of Search .......... 73/30, 32 R, 32 A, 861.02, 73/861.03

[56] References Cited

U.S. PATENT DOCUMENTS 3,043,138  7/1962  Waugh .
3,201,987  8/1965  Ackerman .
3,958,447  5/1976  Baker et al. ......................... 73/32 R
4,196,613  4/1980  Cole .................................... 73/32 R
4,333,355  6/1982  Dacus et al. ........................ 73/32 R Primary Examiner—John Chapman
Attorney, Agent, or Firm—Christie, Parker & Hale

[57] ABSTRACT

A freely rotatable turbine is placed in the path of flowing fluid to drive the turbine at an angular velocity that, at steady state, is dependent upon the linear velocity of the flowing fluid. A transient condition is created in the angular velocity of the turbine. The time constant of the transient condition is determined. The time constant is representative of the density of the flowing fluid—the shorter the time constant, the higher the density and vice versa. The transient condition is created by disturbing the free rotation of the turbine, namely, by imnpairing free rotation to reduce the angular velocity of the turbine to zero, and then permitting the turbine to return to free rotation.

8 Claims, 2 Drawing Sheets

METHOD AND APPARATUS FOR MEASURING FLUID DENSITY

This is a continuation of application Ser. No. 07/046,138 filed May 4, 1987, which is a continuation-in-part of application Ser. No. 06/811,719 filed Dec 20, 1985, both abandoned.

BACKGROUND OF THE INVENTION

This invention relates to measurement of fluid flow characteristics and, more particularly, to a method and apparatus for measuring the density of flowing fluid and, optionally, if desired, the mass flow rate of the fluid.

In the process control field, there is a need to measure density of a fluid. A device for accomplishing this result is called a densitometer or a densimeter. Generally, fluid density is determined in one of two ways—inferentially or directly. To determine density inferentially, the fluid mass and its volume are measured and density is computed from these measurements. To determine density directly, a parameter related to density by physical law, such as buoyancy, momentum, radiation attenuation, or sonic velocity is measured. A densitometer based on buoyancy typically employs a float and an electrical transducer for sensing the float's displacement. A densitometer based on momentum typically employs a bendable arm disposed transverse to the flow stream and a strain gage to sense the arm's deflection.

One important application for a densitometer is to measure mass flow rate. For example, for petroleum custody transfer and mixing of ingredients in a chemical or physical process, mass flow rate is usually the determinative parameter. A turbine flow meter, as well as a number of other types of flow meters, measure volumetric flow rate. In a turbine flow meter, the angular velocity of the turbine closely tracks the velocity of the fluid driving the turbine blades and is thus representative of the volumetric flow rate. Because the turbine is journaled for rotation on low friction bearings, it absorbs very little of the energy of the flowing fluid and thus therefore responds rapidly to changes in volumetric flow rate. A mass flow rate of a fluid is equal to its volumetric flow rate times its density. Fluid density, in turn, is dependent upon temperature and pressure, particularly when the fluid is a gas. Accordingly, it is necessary to determine fluid density in order to provide an accurate indication of mass flow rate with a turbine flow meter.

SUMMARY OF THE INVENTION

Briefly, the invention utilizes the ability of a turbine flow meter to absorb energy from flowing fluid to measure fluid density. In addition to providing an accurate density measurement, the invention also facilitates the determination of mass flow rate because the same turbine flow meter can be used to measure fluid density and volumetric flow rate.

Broadly, a freely rotatable turbine is placed in the path of flowing fluid to drive the turbine at an angular velocity that, at steady state, is dependent upon the linear velocity of the flowing fluid. A transient condition is created in the angular velocity of the turbine. The time constant of the transient condition is determined The time constant is representative of the density of the flowing fluid—the shorter the time constant, the higher the density and vice versa. In other words, the energy absorbed by the turbine, which is reflected by the time constant of the transient condition, is representative of the fluid density In the preferred embodiment, the transient condition is created by disturbing the free rotation of the turbine, namely, by impairing free rotation to reduce the angular velocity of the turbine to zero, and then permitting the turbine to return to free rotation.

Preferably, the time constant is determined by generating pulses having a period that is inversely proportional to the angular velocity of the turbine and measuring the time intervals between selected pairs of these pulses. Specifically, the time interval is measured between a first given number of the generated pulses beginning at a first point in time during the transient period. The time interval is measured between a second given number of the generated pulses beginning at a second point in time during the transient period. The time interval is measured between a third given number of the generated pulses at steady state. Finally, the time interval is measured between the first and second points in time. From the foregoing measurements, the time constant, and thus the fluid density, is calculated.

A feature of the invention is the use of a single turbine flow meter alternately on a time-shared basis to measure density during a transient condition and flow rate during a steady-state condition.

BRIEF DESCRIPTION OF THE DRAWINGS

The features of specific embodiments of the best mode contemplated of carrying out the invention are illustrated in the drawings in which.

DETAILED DESCRIPTION OF THE SPECIFIC EMBODIMENTS

Figure 1:
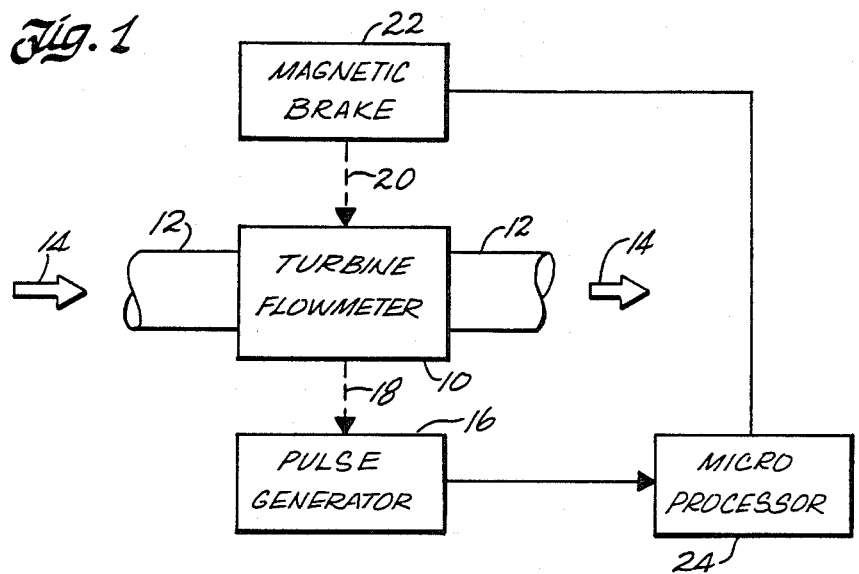
FIG. 1 is a schematic block diagram of apparatus for practicing the invention.

In FIG. 1, a conventional turbine flow meter 10 is connected in a fluid line 12 through which a fluid, represented by arrows 14, flows. By way of example, flow meter 10 could have a turbine that occludes substantially the entire flow path through line 12, such as shown in Potter U.S. Pat. No. 2,270,141, or function as a probe that intercepts only part of the flow, as shown in Guthrie et al U.S. Pat. No. 4,111,043 or Guthrie U.S. Pat. No. 4,134,298. The disclosures of these patents are incorporated fully herein by reference. Part of flow meter 10 is a pulse generator 16, which is magnetically coupled to the turbine blades of flow meter 10 as represented by a dashed line 18. The turbine blades are made of a magnetic material that induces pulses in a pickoff coil in the pulse generator as the blades pass by. As the turbine of flow meter 10 rotates, pulse generator 16 produces one pulse per turbine blade. These pulses have a period that is inversely proportional to the angular velocity of the turbine. As represented by a dashed line 20, a magnetic brake 22 is magnetically coupled to the turbine of flow meter 10. The output of pulse generator 16 is electrically connected to a microprocessor 24. Microprocessor 24 is electrically connected to magnetic brake 22 to actuate same.

In operation, microprocessor 24 first actuates magnetic brake 22 to reduce the angular velocity of the flow meter turbine to zero. Then microprocessor 24 releases brake 22 permitting the flow meter turbine to return to a steady state angular velocity that is dependent upon the linear velocity of the fluid flowing through line 12. The release of brake 22 creates a transient condition in the angular velocity of the flow meter turbine as it returns to the steady state angular velocity. By monitoring the pulses generated by pulse generator 16 during the steady state and transient conditions, microprocessor 24 determines the time constant of this transient condition, which is representative of the density of the fluid flowing through line 12.

Figure 2:
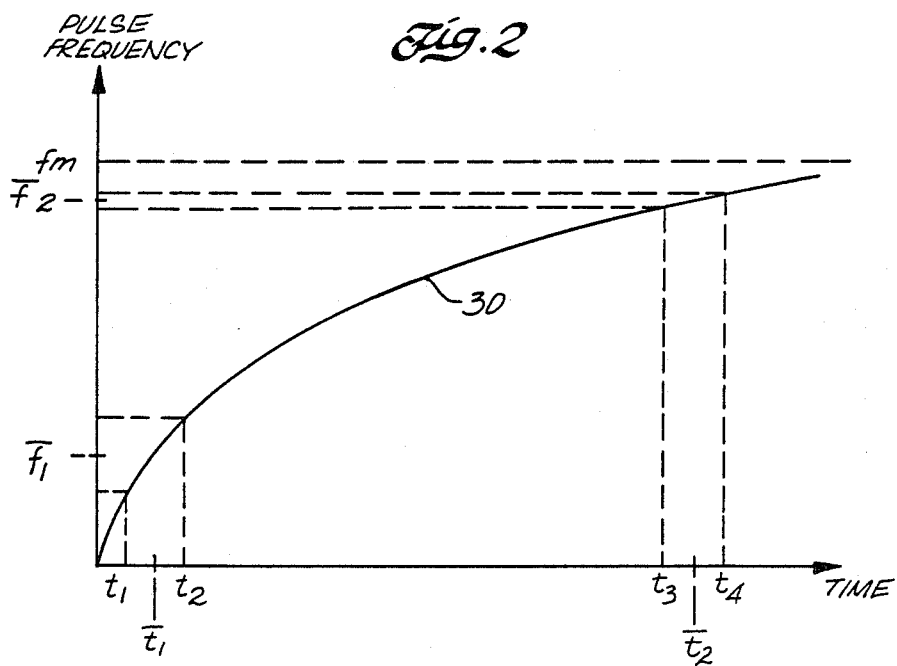
FIG. 2 is a graph illustrating a preferred technique for determining the time constant of the transient condition.

Reference is made to FIG. 2 in connection with an explanation of the preferred technique for determining the time constant. In FIG. 2, the ordinate represents pulse frequency, the abscissa represents time and an exponential curve 30 represents the rise of the angular velocity of the turbine rotor from standstill, i.e., zero toward steady state, that is, curve 30 represents the transient condition of the angular velocity. Curve 30 is represented by the equation.

$$f = f_m(1 - e^{-t/\tau}) \tag{1}$$

where f is the dependent variable, i.e., the instantaneous frequency of the pulses from pulse generator 16, $f_m$ is the steady state frequency of pulses from pulse generator 16, e is the base of natural logarithms, t is the independent variable time, and $\tau$ is the time constant. The average frequency at two locations on curve 30 are first determined. Since frequency is the reciprocal of the period, $$\bar{f}_1 = \frac{N}{t_2 - t_1} \tag{2}$$

$$\bar{f}_2 = \frac{N}{t_4 - t_3} \tag{3}$$

where $\bar{f}_1$ is the average frequency at one location on curve 30, $\bar{f}_2$ is the average frequency at the other location on curve 30, N is the number of blades on the flow meter turbine, $t_1$ is a point in time shortly after release of magnetic brake 22 (at the beginning of the one location on curve 30), $t_2$ is the point in time one revolution of flow meter turbine after $t_1$, i.e., N pulses after $t_1$, $t_3$ is a point in time an arbitray number of revolutions of the flow meter turbine after $t_2$ (at the beginning of the other location on curve 30), and $t_4$ is the point in time one revolution after $t_3$, i.e., N pulses after $t_3$. From inspection of FIG. 2, it can be seen that $$\bar{t}_1 \approx \frac{t_2}{2} \tag{4}$$

$$\bar{t}_2 = \frac{t_3 + t_4}{2} \tag{5}$$

$\bar{t}_1$ is the average time of occurrence of $\bar{f}_1$, assuming that $t_2$ is much larger than $t_1$, and $\bar{t}_2$ is the average time of occurrence of $\bar{f}_2$.

When the flow meter turbine is at rest pulse generator 16 generates no pulses. Thus, it is difficult to determine the zero point on curve 30. For this reason, $t_1$ is taken as the reference point for the calculations performed by microprocessor 24 and the variable t is measured from $t_1$. Rearranging equation (1) and using time $t_1$ as the reference results in the equation $$\frac{t_1 + t}{\tau} = -\ln\left(1 - \frac{f}{f_m}\right) \tag{6}$$

Substituting $\bar{f}_1$ for the variable f and $\bar{t}_1$ for the variable t yields the following equation $$\frac{t_1 + \bar{t}_1}{\tau} = -\ln\left(1 - \frac{\bar{f}_1}{f_m}\right) = K_1 \tag{7}$$

where $K_1$ is a constant introduced for simplicity. Substituting $\bar{f}_2$ for the variable f and $\bar{t}_2$ for the variable t yields the equation $$\frac{t_1 + \bar{t}_2}{\tau} = -\ln\left(1 - \frac{\bar{f}_2}{f_m}\right) = K_2 \tag{8}$$

where $K_2$ is a constant introduced for simplicity.

Solving equations (7) and (8) for the time constant $\tau$, yields the equation $$\tau = \frac{\bar{t}_2 - \bar{t}_1}{K_2 - K_1} = \frac{t_3 + t_4 - t_2}{2(K_2 - K_1)} \tag{9}$$

which expresses $\tau$ in terms of the measured values $t_2$, $t_3$, $t_4$, and $f_m$. During steady state immediately prior to actuation of brake 22 $f_m$ is determined by measuring the time interval between N pulses from pulse generator 16. Then during the transient condition, $t_2$, $t_3$, and $t_4$ are measured. Microprocessor 24 solves equation (9) for the time constant, which is representative of the density of the fluid in line 12. Since the measured value $f_m$ also represents volumetric flow rate, no further measurements need to be made to compute mass flow rate.

Figure 3:
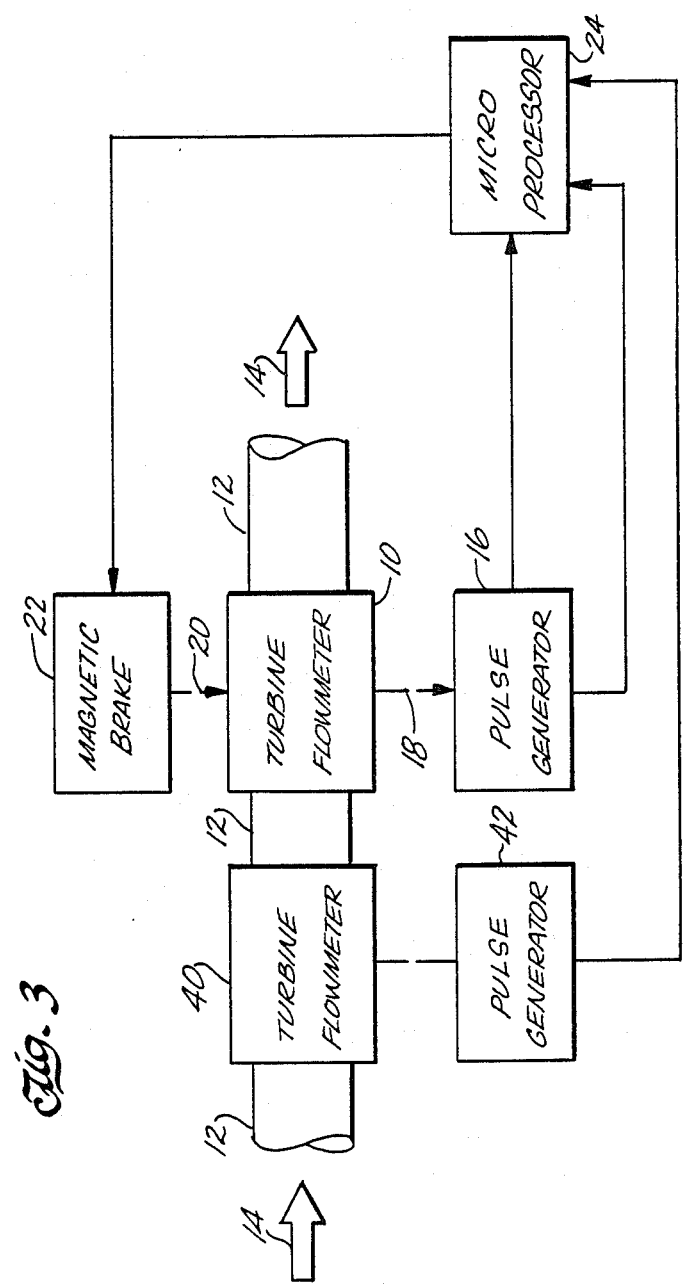
FIG. 3 is a schematic block diagram of an alternative embodiment of apparatus for practicing the invention.

Reference is made to FIG. 3, in which components in common with the embodiment of FIG. 1 are identified with the same reference numerals. In this embodiment, a separate turbine flow meter 40 is installed in line 12 to measure the volumetric flow rate. Flow meter 40 includes a conventional pulse generator 42 that produces a pulse each time one of the turbine blades of flow meter 40 passes during rotation. The output of pulse generator 42 is connected to microprocessor 24, which computes mass flow rate and/or fluid density as described above.

Broadly, the invention creates a transient condition in the angular velocity of a flow meter turbine disposed in a flowing fluid and determining the time constant of the transient condition. Preferably, the transient condition is created by disturbing the free rotation of the flow meter turbine as disclosed. However, the transient condition could alternatively be created by disturbing the flow rate, i.e., by abruptly changing the flow rate from one value to another and determining the time constant as the angular velocity of the turbine responds to the abrupt change in flow rate. Instead of determining the time constant of the transient condition after the brake is released as disclosed, the time constant could be determined during the braking interval, i.e., as the brake is being applied, although this requires that the braking force remain constant during its application. Alternatively, instead of a brake, a motor could be employed to speed up the flow meter turbine, in this case the time constant of the transient condition could be either measured during the speed up interval or during the return interval, after the motor stops driving the flow meter turbine. Another alternative is to employ a turbine having flat blades, i.e., blades that do not rotate responsive to axial fluid flow through the line and retractable but stationary swirl vanes; when the swirl vanes are retracted, the turbine is stationary in its steady-state condition. To introduce a transient condition, the swirl vanes are injected into the line thereby creating helical fluid flow which drives the flat-bladed turbine. If a probe-type turbine flow meter is employed, the transient condition can be created by rotating the probe 90° to the flow stream or gating the turbine chamber closed as disclosed in above-referenced U.S. Pat. Nos. 4,111,043, or 4,134,298.

If the transient response of the turbine follows a different characteristic curve not represented by an exponential function, the same principles apply. The characteristics of the curve are measured to determine the constant(s), which is representative of fluid density.

Attached as appendix A is a source code listing in Turbo Pascal language of the preferred program executed in microprocessor 24. The flowmeter density constant from which the fluid density is derived from the calculated time constant can be determined in numerous ways. One such way is to first operate the densitometer using a fluid of known density to determine the flow meter density constant.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention.

APPENDIX A

```
(*
 * densitometer
 *
 * This program demonstrates a method of determining fluid density
 * based on analysis of the transient characteristics of a turbine
 * flowmeter.
 *
 * 5/21/85 shs
 *
 *)

program densitometer;

{constants} const
    flowmeter_density_constant = 1.0;
    maximum_number_of_data_points = 2000;
    one_second = 1.0;
    running    = false;

{types of data} type
    time      = real;
    frequency = real;

data_point_information = record
        time_of_blade: time;
        average_freq:  frequency;
        time_of_freq:  time;
    end;

{variables - working storage} var
    data_point:              array [1..maximum_number_of_data_points]
                             of data_point_information;

number_of_data_points:   integer;

brake_controller:        (braking, released);

blade_detector:          (blade_present, no_blade);
```

```
maximum_freq:          frequency;
F1:                    frequency;
F2:                    frequency;
T1:                    time;
T2:                    time;
tau:                   real;
density:               real;
   }

(*
 * Hardware control procedures
 *
 *     apply_brake        - bring the turbine down to a stop
 *     release_brake      - let the turbine start moving
 *     wait_for_next_blade. - waits until the next turbine blade is present
 *
 *)

procedure apply_brake;
begin
    brake_controller := braking;
end;

procedure release_brake;
begin
    brake_controller := released;
end;

procedure wait_for_next_blade;
begin
    repeat until blade_detector = blade_present;
    blade_detector := no_blade;
end;

(*
 * Realtime clock procedures
 *
 *     time_of_day    - returns the time of day in seconds since the epoch
 *     delay_1_second - waits for 1 second and then returns
 *
 *)

function time_of_day: time;
begin
end;

procedure delay_1_second;
var
    current_time: time;
    end_of_delay: time;

begin
    end_of_delay := time_of_day + one_second;

repeat
        current_time := time_of_day
    until current_time >= end_of_delay;
end;
(*
 * capture_turbine_data - This procedure records the actual time
 *                         of each blade crossing for about 2 seconds.
 *
 *)

procedure capture_turbine_spinup_data;
var
```

```
       current_data_point:  integer;
       end_of_capture:      time;
   begin
       end_of_capture := time_of_day + 2 * one_second;
       current_data_point := 0;

repeat
          wait_for_next_blade;

current_data_point := current_data_point + 1;

with data_point[current_data_point] do
             time_of_blade := time_of_day;

until (time_of_day >= end_of_capture) or
             (current_data_point = maximum_number_of_data_points);

number_of_data_points := current_data_point;
   end;
* calculate_frequencies - This procedure finds the average frequency
*                         at each data point, and interpolates to find
*                         the time at which that frequency was present.
*)

procedure calculate_frequencies;
var
    i:  integer;

begin

{calculate the average frequency for each interval} data_point[1].average_freq := 0;
    for i := 2 to number_of_data_points do
       data_point[i].average_freq :=
           1.0 / (data_point[i].time_of_blade - data_point[i-1].time_of_blade);

{calculate the time at which this frequency occured (linear approximation)} data_point[1].time_of_freq := 0;
    for i := 2 to number_of_data_points do
       data_point[i].time_of_freq :=
           (data_point[i].time_of_blade + data_point[i-1].time_of_blade) / 2.0;

{determine maximum frequency as frequency of last data point} maximum_freq := data_point[number_of_data_points].average_freq;

{decide what data points to use for the calculations}

T1 := 0;
    F1 := 0;
    T2 := 0;
    F2 := 0;

for i := 1 to number_of_data_points do
    begin
       if (T1 = 0) and (data_point[i].average_freq >= (maximum_freq * 0.20)) then
       begin
          T1 := data_point[i].time_of_freq;
          F1 := data_point[i].average_freq;
       end;
```

```
          if (T2 = 0) and (data_point[i].average_freq >= (maximum_freq * 0.80)) then
          begin
              T2 := data_point[i].time_of_freq;
              F2 := data_point[i].average_freq;
          end;
       end;

end;

*   calculate_tau - This procedure uses the selected time and frequency
*                  data to determine the "time constant" tau, of the
*                  turbine flowmeter.  This time constant indicates the
*                  flowing density of the fluid.
*)

procedure calculate_tau;
var
    K1:   real;
    K2:   real;
    T0:   time;

begin
    K1 := 1.0 / ln(1.0 - F1 / maximum_freq);
    K2 := 1.0 / ln(1.0 - F2 / maximum_freq);
    T0 := (T1 * K2 - T2 * K1) / (K2 - K1);
    tau := -(T2 + T0) * K2;
end;

procedure calculate_density;
begin

{what is the relationship between tau and density?}
    density := flowmeter_density_constant / tau;

end;

* Main program - The main program repeatedly brakes, captures and calculates.
*
*)

begin {main program} while running do
    begin
        apply_brake;
        delay_1_second;
        release_brake;
        capture_turbine_spinup_data;
        calculate_frequencies;
        calculate_tau;
        calculate_density;
    end;

end.
```

What is claimed is:

1. A method for measuring the density of a flowing fluid comprising the steps of:
   placing a freely rotatable turbine in the path of the flowing fluid to drive the turbine at a steady state angular velocity that is dependent upon the linear velocity of the flowing fluid;
   creating a transient condition in the angular velocity of the turbine; and
   determining the time constant of the transient condition, whereby said time constant is indicative of the density of the fluid.

2. The method of claim 1, in which the creating step comprises disturbing the free rotation of the turbine.

3. The method of claim 1, in which the creating step comprises reducing the angular velocity of the turbine.

4. The method of claim 3, in which the determining step comprises:

generating pulses having a period that is inversely proportional to the angular velocity of the turbine;

measuring the time interval between a first given number of the generated pulses beginning at a first point in time during the transient condition;

measuring the time interval between a second given number of the generated pulses beginning at a second point in time during the transient condition;

measuring the time interval between a third given number of the generated pulses at steady state; and measuring the time interval between the first and second points in time.

5. The method of claim 4, in which the turbine has N blades and the first, second, and third given number of pulses are all N.

6. A densitometer comprising:

a flow meter having a freely rotatable turbine and means for sensing the angular velocity of the turbine;

means for creating a transient condition in the angular velocity of the turbine; and means for determining the time constant of the transient condition, whereby said time constant is indicative of the density of a flowing fluid.

7. The densitometer of claim 6 in which the means for creating a transient condition comprises means for reducing the angular velocity of the turbine to zero and then releasing the turbine.

8. The densitometer of claim 7, in which the means for sensing the angular velocity of the turbine comprises means for generating pulses having a period that is inversely proportional to the angular velocity of the turbine and the means for determining the time constant of the transient condition comprises:

means for measuring the time interval between a first given number of the generated pulses beginning at a first point in time during the transient condition;

means for measuring the time interval between a second given number of the generated pulses beginning at a second point in time during the transient condition;

means for measuring the time interval between a third number of the generated pulses at steady state; and means for measuring the time interval between the first and second points in time.

* * * * *